United States Patent
Buchanan et al.

(10) Patent No.: US 7,763,265 B2
(45) Date of Patent: Jul. 27, 2010

(54) UV BARRIER FORMULATION FOR POLYESTERS

(75) Inventors: Karl H. Buchanan, Kure Beach, NC (US); Helen J. Codd, Wilmington, NC (US); Peter S. Kezios, Wilmington, NC (US)

(73) Assignee: Dak Americas, LLC, Charlotte, NC (US)

( * ) Notice: Subject to any disclaimer, the term of this patent is extended or adjusted under 35 U.S.C. 154(b) by 1137 days.

(21) Appl. No.: 10/879,160

(22) Filed: Jun. 30, 2004

(65) Prior Publication Data

US 2006/0002867 A1 Jan. 5, 2006

(51) Int. Cl.
*A61K 9/00* (2006.01)
*A61Q 17/04* (2006.01)

(52) U.S. Cl. .......................................... 424/402; 424/59
(58) Field of Classification Search ........................ None
See application file for complete search history.

(56) References Cited

U.S. PATENT DOCUMENTS

| | | | |
|---|---|---|---|
| 4,399,265 A | 8/1983 | Garware et al. | |
| 6,316,531 B1 | 11/2001 | Garware et al. | |
| 6,392,005 B1 | 5/2002 | Jen | |
| 6,489,434 B2 | 12/2002 | Jen | |
| 6,602,447 B2 | 8/2003 | Danielson et al. | |
| 6,783,827 B2 | 8/2004 | Jen | |
| 2003/0075709 A1* | 4/2003 | Danielson et al. | 252/588 |
| 2003/0151027 A1 | 8/2003 | Zhao et al. | |
| 2003/0186040 A1 | 10/2003 | Oya | |

FOREIGN PATENT DOCUMENTS

| | | |
|---|---|---|
| RU | 2 188 832 C2 | 9/2002 |
| SU | 695561 | 10/1979 |

OTHER PUBLICATIONS

"Opportunities for Improving the Quality of Consumer Products with the Use of UV Absorbers in PET Packaging", Milliken Chemical, www.packagingdigest.com/whitepaper/track.php?id=27, 2003, pp. 1-10.
Chemistry Encyclopedia, M., Bolshaya Rossiyskaya Enciclopedia, 1995, v. 4, pp. 1-14.

* cited by examiner

*Primary Examiner*—Johann R Richter
*Assistant Examiner*—Frank I Choi
(74) *Attorney, Agent, or Firm*—Oblon, Spivak, McClelland, Maier & Neustadt, L.L.P.

(57) ABSTRACT

The invention provides UV-barrier formulations which result in products which effectively resist the transmission of ultraviolet light therethrough. The invention also provides UV-barrier formulations which result in products with improved resistance to ultraviolet light. In particular, the invention provides UV barrier formulations for polyester resins that have improved resistance to ultraviolet radiation, and significantly reduce ultraviolet light transmission in the resulting resin products. The invention also provides products and manufacturing processes based on the above formulations.

27 Claims, 1 Drawing Sheet

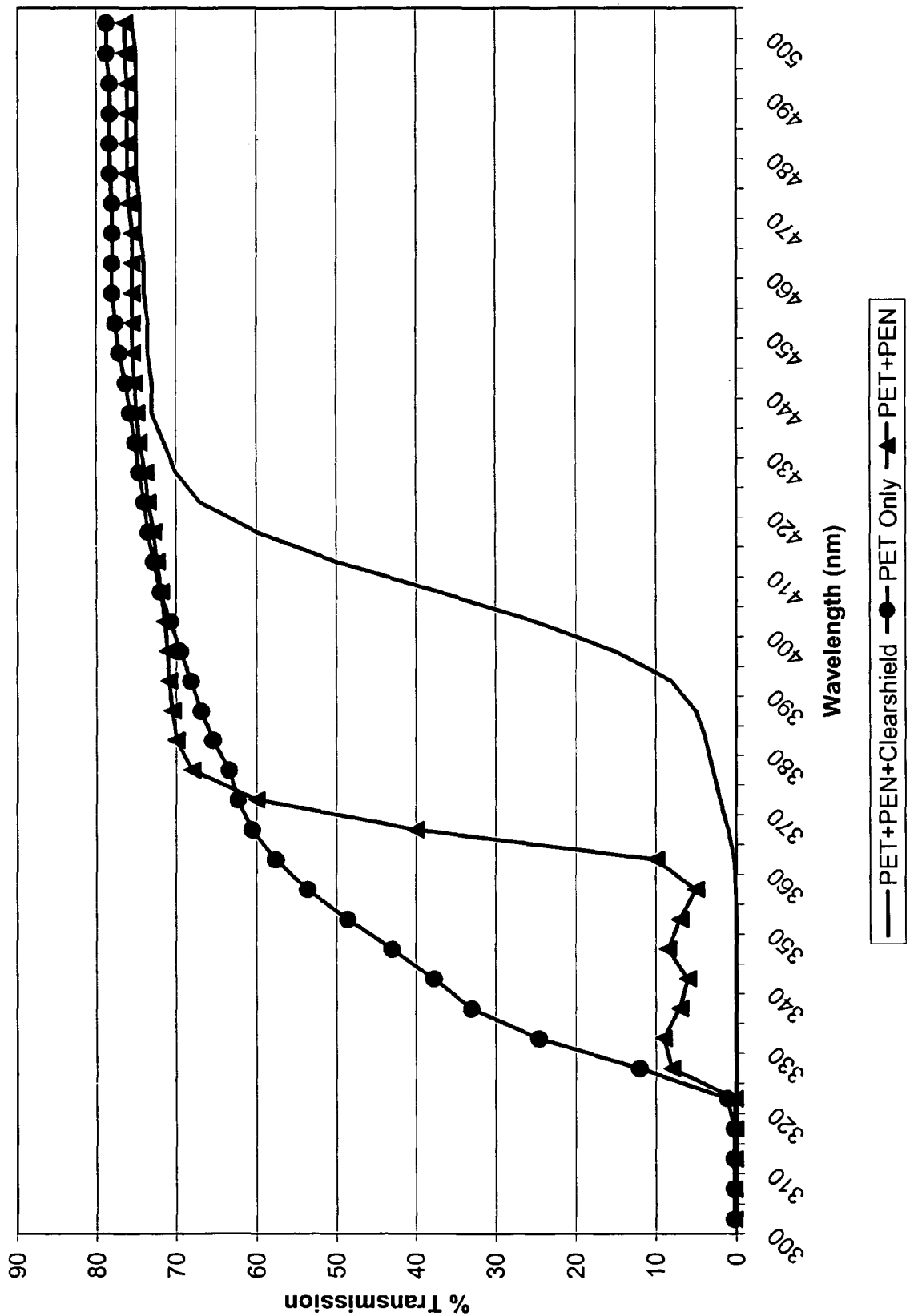

UV BARRIER FORMULATION FOR POLYESTERS

FIELD OF THE INVENTION

The invention relates to UV-barrier formulations which result in products which effectively resist the transmission of ultraviolet light therethrough. The invention also relates to UV-barrier formulations which result in products with improved resistance to ultraviolet light. In particular, the invention relates to UV barrier formulations for polyester resins that have improved resistance to ultraviolet radiation, and significantly reduce ultraviolet light transmission in the resulting resin products.

BACKGROUND OF THE INVENTION

Sunlight and conventional indoor lighting comprises energy in the visible range and in the ultraviolet (UV) range. The ultraviolet component, especially radiation ranging from 200 nm to 400 nm, is primarily responsible for the degradation of organic matter, including polymeric products and food products. Such food products are typically contained in packaging composed of one or more polymeric components. Thus, it is desirable that the polymeric packaging materials minimize, as much as possible, the transmission of ultraviolet light. Polyester resins are widely used in packaging materials due to their excellent clarity and transparency. Polyesters are subject to degradation by ultraviolet light and will transmit UV light. Ultraviolet absorbers are added to polyester formulations to increase the resistance of the final resin product to UV degradation, and to decrease the transmission of ultraviolet light through the final product but maintain the transmission of visible light.

As the use of polyester packaging, and in particular, PET (polyethylene terephthalate), continues to grow, more and more foods and drinks are now being packaged in polyester-based resins. As mentioned above, some of the ingredients in food and drink items are susceptible to degradation by UV light from the sun and from grocery/convenience store lighting. Such degradation can result in changes in color, flavor or nutritional value of the contents of the packaging. Polyethylene terephthalate with no UV absorber will protect against UV light by providing around 10% transmission at about 320 nm wavelength.

In the last few years, chemical additive suppliers and PET producers have begun selling products that block UV light, and reduce the harmful exposure that degrades PET containers, and the contents within these containers. These additives can be incorporated at an injection molding step. PET producers are also incorporating these same commercial additives or proprietary formulations directly into their processes. This invention relates to formulations that provide end products that significantly reduce UV transmission therethrough, and more reliably withstand the effect of UV radiation without significant degradation or deterioration. These formulations or compositions also offer an alternative supply option to those that wish to convert to the use of PET containers from other conventionally UV resistant polymer based containers.

SUMMARY OF THE INVENTION

It is an object of the invention to provide UV-barrier formulations for polyester resins, which results in products which effectively resist the transmission therethrough of ultraviolet light.

It is another object of the invention to provide UV-barrier formulations for polyester resins, which result in products with improved resistance to ultraviolet light.

It is another object of the invention to provide polyester formulations which result in products which effectively resist the transmission therethrough of ultraviolet light.

It is another object of the invention to provide polyester formulations which result in products with improved resistance to ultraviolet light.

It is another object of the invention to provide a process for the manufacture of UV-barrier formulations which result in products with improved resistance to ultraviolet light.

It is another object of the invention to provide a process for the manufacture of UV-barrier formulations which result in products which effectively resist the transmission therethrough of ultraviolet light.

It is another object of the invention to provide a process for the manufacture of polyester resins which result in products with improved resistance to ultraviolet light.

It is another object of the invention to provide a process for the manufacture of polyester resins which result in products which effectively resist the transmission therethrough of ultraviolet light.

It is a further object of the present invention to provide a process which will homogeneously mix the polyester material and the UV-barrier formulation so that they will reliably stay together uniformly during the mixing process and thereafter.

It is a further object of the present invention to provide polyester products which effectively resist the transmission therethrough of ultraviolet light.

It is a further object of the present invention to provide polyester products which exhibit an exceptional resistance to UV radiation.

These and other objects of the present invention have been satisfied, either individually or in combinations thereof, by the discovery of a UV-barrier formulation comprising the following components: polyethylene naphthalate (PEN) and a polyoxyalkylene UV absorber (such as CLEARSHIELD UV absorber from Milliken Chemical), by the discovery of a polyester formulation comprising one or more polyesters, polyethylene naphthalate and the polyoxyalkylene UV absorber, and by the products produced by these formulations and the manufacturing processes thereof.

BRIEF DESCRIPTION OF THE DRAWING

Various other objects, features and attendant advantages of the present invention will be more fully appreciated, as the same become better understood from the following detailed description, when considered in connection with the accompanying drawing.

FIG. 1 is a transmission profile comparing a preferred formulation of the invention with other conventional formulations.

DETAILED DESCRIPTION OF THE PREFERRED EMBODIMENTS

The present invention relates to UV-barrier formulations comprising polyethylene naphthalate (PEN) and a polyoxyalkylene UV absorber, and polyester formulations comprising one or more polyesters, polyethylene naphthalate and a polyoxyalkylene UV absorber (or CLEARSHIELD). These formulations blend a polyoxyalkylene based UV absorber with a PEN component to reduce UV transmission to around 10% at UV wavelengths up to about 390 nm. The advantages of these formulations are both economical and functional. The PEN is the less costly additive, but it only provides UV protection up to about 360 nm, with little UV absorbance effect at higher wavelengths. CLEARSHIELD (a preferred polyoxyalkylene UV absorber), a more costly additive, can provide protection from about 360 nm to about 390 nm. The use of PEN to provide UV protection at lower wavelengths provides a significant cost saving versus using only CLEARSHIELD, by permitting the use of less CLEARSHIELD than normally needed in order to obtain the same level of UV absorbance for the overall composition. The use of both of these additives together, provides a very economical formulation with an unexpected improvement in UV resistance, above what would be expected based on the combination of these additives. In particular, one improvement seen is an increase in the level of UV absorbance up to about 390 nm when the PEN and polyoxyalkylene UV absorber are combined, even though only one of the components actually has a significant measurable absorbance at 390 nm. Thus, while one might expect some absorbance at 390 nm due to the polyoxyalkylene UV absorber component, the level of absorbance would be expected to be significantly lower, as the PEN does not normally absorb at that wavelength. The present inventors have found, however, that by combining the two UV absorbing components, there is a significant increase in absorbance at about 390 nm (i.e. significant reduction in UV transmission at about 390 nm) that would not be present using either component alone.

While the present inventors do not wish to be bound by any particular theory on the mechanism of action for the present invention, it appears that there is either an interaction or an actual chemical reaction, for example, the formation of a chemical bond, between the PEN and polyoxyalkylene UV absorber components (and possibly an interaction or chemical reaction with either or both of these components and the polyester matrix) that causes the UV absorbance at wavelengths up to about 390 nm to significantly increase at a given level of the UV absorber.

The formulations of the invention may be prepared in the melt state using conventional techniques known in the art, including melt extrusions from batch, semi-continuous or continuous. It is preferable to add the polyoxyalkylene UV absorber as late as possible in the melt process due to its potential sensitivity to discoloration.

In one embodiment of the invention, a composition comprising a polyester matrix is prepared having an amount of UV absorbing composition sufficient to provide a UV transmission of about 20% or less at about 390 nm, and where the UV absorbing composition comprises polyethylene naphthalate (PEN) and the polyoxyalkylene UV absorber. In another embodiment, the above composition provides a UV transmission of about 15% or less, more preferably 10% or less, and even more preferably 5% or less, at about 390 nm.

In another preferred embodiment of the invention about 1000 ppm (0.1 wt %) CLEARSHIELD and about 0.2 wt % PEN are mixed with a polyester matrix comprises predominantly PET. The amounts of these components are based on the total weight of the polyester formulation or composition. This combination provides UV protection in the PET product, and also provides an economical UV barrier with good appearance in the final product. It has been determined that adding more than 0.2% PEN will not further improve the UV barrier of PET, but adding less than 0.1% will reduce the UV barrier. The equivalent UV barrier of about 10% transmission at about 390 nm, using both PEN and CLEARSHIELD, could be provided by using 2000 ppm CLEARSHIELD without PEN. However, this formulation would considerably increase the cost of providing the same UV barrier protection as the PEN/CLEARSHIELD combination.

In another embodiment of the invention, the additives are incorporated into a polyester resin, such as PET resin, by injection into the molten polyester in the transfer line, downstream of the last polymerization vessel and upstream of the pelletizers. This injection can occur using a twin screw extruder to melt the PEN polymer and combine it with the polyoxyalkylene UV absorber, for example, liquid CLEARSHIELD 390B or 390R. The molten mixture is then injected into the transfer line using a metering pump. After the PEN/CLEARSHIELD formulation is injected into the polyester melt stream, it is mixed using both dispersive and distributive mixing to ensure a good mix with the PET melt stream. The mixture is then pelletized. The pellets may be solid state polymerized to further raise the intrinsic viscosity (IV) of the resulting resin. This may involve holding the pellets at temperatures above about 200° C. for greater than about 12 hours. The pellets should not degrade or significantly change color during the solid stating process.

In another embodiment, a concentrated masterbatch of PEN and the polyoxyalkylene UV absorber is produced and then dry blended with a polyester resin.

The UV absorber of the present invention is a polymeric UV absorber having various chain lengths of polyoxyalkylenes, as described in U.S. Pat. No. 6,602,447, the contents of which are hereby incorporated by reference. Within the context of the present invention, the UV absorber as described in U.S. Pat. No. 6,602,447 is denoted herein as a "polyoxyalkylene UV absorber", although it may contain other types of groups in the backbone of the polymeric compound, with oxyalkylene groups being present with at least 6 total moles of oxyalkylene units per molecule of UV absorber, as in the above noted '447 patent. An embodiment of the polyoxyalkylene UV absorber of the present invention is that described in the '447 patent, which is an ultraviolet compound conforming to the structure represented by Formula (I)

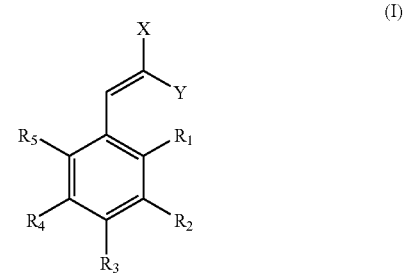

(I)

wherein $R_1$, $R_2$, $R_3$, $R_4$, and $R_5$ are the same or different and are selected from the group consisting of $C_{1-20}$ alkyl, halo, hydroxyl, hydrogen, cyano, sulfonyl, sulfo, sulfato, aryl, nitro, carboxyl, $C_{1-20}$ alkoxy, and B-A, wherein at least one of $R_1$, $R_2$, $R_3$, $R_4$ and $R_5$ is B-A wherein B is selected from the group consisting of N, O, S, $SO_2$, $SO_3$, $CO_2$, and A is represented by the Formula (II)

[polyoxyalkylene constituent]$_2$R'  (II)

wherein 'polyoxyalkylene constituent' is selected from the group consisting of at least three monomers of at least one $C_{2-20}$ alkyleneoxy group, glydicol, glycidyl, or mixtures thereof, R' is selected from the group consisting of hydrogen, $C_{1-20}$ alkoxy, $C_{1-20}$ alkyl, and $C_{1-20}$ esters; wherein if B is N, then Z is 2, and if B is other than N, then Z is 1; X and Y are the same or different and are selected from the group consisting of hydrogen, cyano, C(O)OR, C(O)R, C(O)NR"R''', $C_{1-20}$ alkyl, and $C_{1-20}$ alkoxy, or X and Y are combined to form a ring system, and R, R", and R''' are defined as above for any of $R_1$, $R_2$, $R_3$, $R_4$, and $R_5$; and wherein if X and Y are not combined to form a ring system then at least one of said X and Y is either cyano or hydrogen. A preferred embodiment of the UV absorber is a commercially available product tradenamed CLEARSHIELD (available from Milliken), most preferably CLEARSHIELD 390B or 390R.

The polyesters of the invention may include, but are not limited to, polyester synthesized from aliphatic, aromatic or cyclic (aliphatic or aromatic) dicarboxylic acids, or an aliphatic, aromatic or cyclic (aliphatic or aromatic) ester, with an aromatic, aliphatic or cyclic (aliphatic or aromatic) diol; or an esters prepared from two or more aliphatic, aromatic or cyclic (aliphatic or aromatic) esters. Examples of polyesters include, but are not limited to, polyethylene terephthalate, polyethylene naphthalate, polyethylene isophthalate, polypropylene terephthalate, polybutylene terephthalate, poly(1,4-cyclohexylene dimethylene terephthalate) and polyethylene-2,6-naphthalene dicarboxylate, and mixtures thereof. Copolymers, blends and mixtures thereof are also included. Preferred embodiments of the present invention use polyethylene terephthalate polymers having copolymerized therewith from 0 to 5 wt % of isophthalic acid (or the dialkyl isophthalate counterpart, depending on whether the polyester is produced from a terephthalic acid or dimethyl (or dialkyl) terephthalate based process) and from 1 to 3 wt % of diethylene glycol. Such copolymers are commonly used as resins for the formation of various bottles and other containers, most commonly in the production of soda bottles.

The term "polyesters," "polyester matrix" or "polyester resins," as used herein, refers to all of the above, and includes polyesters prepared from one or more monomers, and blends of one or more of such polyesters.

The term "polymer or polymers," "polymeric" or "resin or resins," as used herein, refers to both homopolymers and copolymers prepared from one or more monomeric constituents, and to crosslinked systems thereof and branched systems thereof, including, but not limited to, grafted systems thereof.

Dicarboxylic acids include, but are not limited to, aromatic dicarboxylic acids, such as terephthalic acid, isophthalic acid, phthalic acid and 2,6-naphthalenedicarboxylic acid; aliphatic dicarboxylic acids, such as adipic acid, azelaic acid, sebacic acid and decanedicarboxylic acid; and alicyclic dicarboxylic acids, such as cyclohexanedicarboxylic acid. Diols include, but are not limited to, aliphatic diols such as 1,4-butanediol, 1,3-propanediol, 1,6-hexanediol, monoethylene glycol, diethylene glycol, triethylene glycol and polyethylene glycol; alicyclic diols, such as 1,4-cyclohexanedimethanol; and aromatic diols such as bisphenol A. These diacids and diols may be used alone or in combination of two or more.

Other polyester components include, but are not limited to, phthalic anhydride, trimellitic acid, pyromellitic acid, dimeric acid and 5-sodiumsulfoisophthalic acid.

The polyesters can be produced by condensation reactions and/or ester exchange reactions, and other methods known in the art.

Products of the invention include, but are not limited to, bottles, various-shaped containers, sheets, films, fibers, tubes, and the like. Products also include packaging materials, such as containers, sheets, blister packages, and the like, which can be utilized for storage purposes. Products of the invention may include one or more polyesters, optionally in combination with one or more different thermoplastics, in any combination.

Other additives may optionally be added to the formulations of the invention to effectuate a desirable physical state. These additives include, but are not limited to solvents, viscosity modifiers, fillers, colorants, acid scavengers, antistatic agents and other UV absorbers. Additives may be added prior to, during, and/or after introduction of the UV-barrier formulation within the desired polyester matrix.

EXAMPLES

Having generally described this invention, a further understanding can be obtained by reference to certain specific examples, which are provided herein for purposes of illustration only, and are not intended to be limiting, unless otherwise specified.

Example 1

Twenty pounds of a PEN/PET copolymer containing 90 wt % polyethylene terephthalate and 10 wt % polyethylene naphthalate were compounded with one pound of CLEARSHIELD 390B (available from Milliken) in a twin screw extruder. The compounded mixture was pelletized into a masterbatch. The masterbatch was dry blended with virgin PET polymer pellets at a 46.6 to 1 letdown ratio and the dry blend was used to injection mold preforms. The preforms were then stretch blow molded. The final concentration of PEN in the bottles was 0.200%. The final concentration of CLEARSHIELD 390B in the bottles was 0.100%.

Transmission testing of the sidewall of the bottles produced demonstrated that at the concentration used this formulation provided UV protection up to 10% transmission at 390 nm.

FIG. 1 is a transmission profile comparing a preferred formulation of the invention with other conventional formulations. The corresponding data for this FIGURE is listed in Table 1.

TABLE 1

| | Transmission % at stated wavelength | | |
|---|---|---|---|
| Wavelength (nm) | (invention) PET/0.2% PEN/0.1% CLEARSHIELD | PET | PET/PEN |
| 300 | 0 | 0.3 | 0.3 |
| 305 | 0 | 0.3 | 0.3 |
| 310 | 0 | 0.3 | 0.2 |
| 315 | 0 | 0.3 | 0.2 |
| 320 | 0 | 1.1 | 0.2 |
| 325 | 0 | 12 | 8 |
| 330 | 0 | 24.6 | 9 |
| 335 | 0 | 33 | 7 |
| 340 | 0 | 37.7 | 6 |
| 345 | 0 | 43 | 8.5 |
| 350 | 0 | 48.6 | 7 |
| 355 | 0.1 | 53.6 | 5 |
| 360 | 0.3 | 57.6 | 10 |
| 365 | 1 | 60.5 | 40 |
| 370 | 2 | 62.3 | 60 |
| 375 | 2.9 | 63.4 | 68 |
| 380 | 3.75 | 65.4 | 70 |
| 385 | 5 | 66.9 | 70.5 |
| 390 | 8 | 68.1 | 70.9 |
| 395 | 15 | 69.5 | 71.1 |
| 400 | 25 | 70.7 | 71.4 |
| 405 | 37 | 72 | 71.9 |

TABLE 1-continued

| | Transmission % at stated wavelength | | |
|---|---|---|---|
| Wavelength (nm) | (invention) PET/0.2% PEN/0.1% CLEARSHIELD | PET | PET/PEN |
| 410 | 50 | 72.8 | 72.4 |
| 415 | 60 | 73.5 | 72.8 |
| 420 | 67 | 74 | 73.5 |
| 425 | 70 | 74.6 | 73.8 |
| 430 | 71.5 | 75.1 | 74.6 |
| 435 | 73 | 75.7 | 74.9 |
| 440 | 73 | 76.3 | 75.2 |
| 445 | 73.5 | 77.1 | 75.4 |
| 450 | 73.5 | 77.6 | 75.5 |
| 455 | 74 | 78 | 75.5 |
| 460 | 74 | 78 | 75.5 |
| 465 | 74.5 | 78 | 75.5 |
| 470 | 74.5 | 78 | 75.9 |
| 475 | 75 | 78.3 | 76.1 |
| 480 | 75 | 78.3 | 76.1 |
| 485 | 75 | 78.3 | 76.1 |
| 490 | 75 | 78.3 | 76.1 |
| 495 | 75 | 78.7 | 76.4 |
| 500 | 75.5 | 78.7 | 76.4 |

Obviously, additional modifications and variations of the present invention are possible in light of the above teachings. It is therefore to be understood, that within the scope of the appended claims, the invention may be practiced otherwise than as specifically described herein.

The invention claimed is:

1. A composition comprising a polyester matrix having therein an amount of UV absorbing composition sufficient to provide a UV transmission of about 20% or less at about 390 nm, wherein the polyester matrix comprises polyethylene terephthalate (PET), and wherein the UV absorbing composition comprises polyethylene naphthalate (PEN) and less than 2000 ppm by weight of a polyoxyalkylene UV absorber conforming to the structure represented by Formula (I)

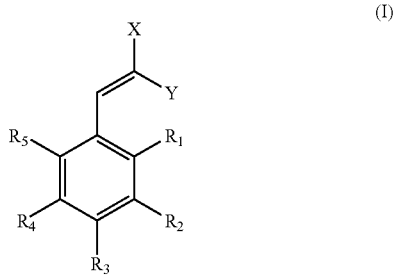

(I)

wherein $R_1$, $R_2$, $R_3$, $R_4$, and $R_5$ are the same or different and are selected from the group consisting of $C_{1-20}$ alkyl, halo, hydroxyl, hydrogen, cyano, sulfonyl, sulfo, sulfato, aryl, nitro, carboxyl, $C_{1-20}$ alkoxy, and B-A, wherein at least one of $R_1$, $R_2$, $R_3$, $R_4$, and $R_5$ is B-A, wherein B is selected from the group consisting of N, O, S, $SO_2$, $SO_3$, $CO_2$, and A is represented by the Formula (II)

[polyoxyalkylene constituent]$_2$R' (II)

wherein 'polyoxyalkylene constituent' is selected from the group consisting of at least three monomers of at least one $C_{2-20}$ alkyleneoxy group, glydicol, glycidyl, or mixtures thereof, R' is selected from the group consisting of hydrogen, $C_{1-20}$ alkoxy, $C_{1-20}$ alkyl, and $C_{1-20}$ esters; wherein if B is N, then Z is 2, and if B is other than N, then Z is 1; X and Y are the same or different and are selected from the group consisting of hydrogen, cyano, C(O)OR, C(O)R, C(O)NR"R'", $C_{1-20}$ alkyl, and $C_{1-20}$ alkoxy, or X and Y are combined to form a ring system, and R, R", and R'" are defined as above for any of $R_1$, $R_2$, $R_3$, $R_4$, and $R_5$; and wherein if X and Y are not combined to form a ring system then at least one of said X and Y is either cyano or hydrogen;

wherein the polyoxyalkylene UV absorber forms either of (i) a chemical bond with or (ii) an interaction with the polyethylene naphthalate.

2. The composition of claim 1, wherein the polyoxyalkylene UV absorber forms a chemical bond with the polyethylene naphthalate.

3. The composition of claim 1, wherein the polyoxyalkylene UV absorber forms an interaction with the polyethylene naphthalate.

4. The composition of claim 1, wherein the polyethylene naphthalate (PEN) is present at about 0.2 wt %, based on the total weight of the composition, and the polyoxyalkylene UV absorber is present at about 0.1 wt %, based on the total weight of the composition.

5. The composition of claim 1, wherein the polyester matrix comprises polyethylene terephthalate having copolymerized therein units obtained from isophthalic acid or dialkylisophthalate.

6. The composition of claim 1, wherein the polyester matrix comprises polyethylene terephthalate having copolymerized therein units obtained from diethylene glycol.

7. The composition of claim 5, wherein the polyester matrix further comprises copolymerized therein units obtained from diethylene glycol.

8. The composition of claim 5, wherein said units obtained from isophthalic acid or dialkylisophtalate are present in an amount of from 0 to 5 wt %, based on total weight of the composition.

9. The composition of claim 6, wherein said units obtained from diethylene glycol are present in an amount of from 1 to 3 wt %, based on total weight of the composition.

10. The composition of claim 7, wherein said units obtained from isophthalic acid or dialkylisophtalate are present in an amount of from 0 to 5 wt %, based on total weight of the composition, and said units obtained from diethylene glycol are present in an amount of from 1 to 3 wt %, based on total weight of the composition.

11. A product prepared from the composition of claim 1 and having a form selected from the group consisting of containers, sheets, films, fibers, tubes.

12. The product of claim 11, wherein the product has a form of a container and said container is a member selected from the group consisting of bottles and blister packages.

13. A method of preparing a composition comprising a polyester matrix having therein a UV absorbing composition, wherein the polyester matrix comprises polyethylene terephthalate (PET), and wherein the UV absorbing composition comprises polyethylene naphthalate (PEN) and a polyoxyalkylene UV absorber, comprising:

mixing the polyethylene naphthalate and the polyoxyalkylene UV absorber to form a UV-barrier formulation, and mixing the UV-bather formulation with the polyester matrix, such that the composition contains less than 2000 ppm by weight of the polyoxyalkylene UV absorber and the polyoxyalkylene UV absorber conforms to the structure represented by Formula (I)

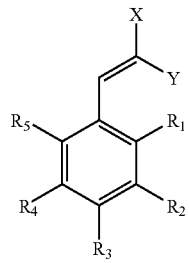

(I)

wherein $R_1$, $R_2$, $R_3$, $R_4$, and $R_5$ are the same or different and are selected from the group consisting of $C_{1-20}$ alkyl, halo, hydroxyl, hydrogen, cyano, sulfonyl, sulfo, sulfato, aryl, nitro, carboxyl, $C_{1-20}$ alkoxy, and B-A, wherein at least one of $R_1$, $R_2$, $R_3$, $R_4$, and $R_5$ is B-A, wherein B is selected from the group consisting of N, O, S, $SO_2$, $SO_3$, $CO_2$, and A is represented by the Formula (II)

[polyoxyalkylene constituent]$_2$R'      (II)

wherein 'polyoxyalkylene constituent' is selected from the group consisting of at least three monomers of at least one $C_{2-20}$ alkyleneoxy group, glydicol, glycidyl, or mixtures thereof, R' is selected from the group consisting of hydrogen, $C_{1-20}$ alkoxy, $C_{1-20}$ alkyl, and $C_{1-20}$ esters; wherein if B is N, then Z is 2, and if B is other than N, then Z is 1; X and Y are the same or different and are selected from the group consisting of hydrogen, cyano, C(O)OR, C(O)R, C(O)NR"R'", $C_{1-20}$ alkyl, and $C_{1-20}$ alkoxy, or X and Y are combined to form a ring system, and R, R", and R'" are defined as above for any of $R_1$, $R_2$, $R_3$, $R_4$, and $R_5$; and wherein if X and Y are not combined to form a ring system then at least one of said X and Y is either cyano or hydrogen.

14. The method of claim 13, wherein the polyethylene naphthalate and the polyoxyalkylene UV absorber are mixed in a twin screw extruder.

15. The method of claim 13, wherein the UV-barrier formulation is mixed with the polyester matrix by injecting the UV-barrier formulation into a melt stream containing the polyester matrix.

16. The method of claim 13, wherein both dispersive and distributive mixing is used to mix the UV-barrier formulation with the polyester matrix.

17. A method of preparing a composition comprising a polyester matrix having therein a UV absorbing composition, wherein the polyester matrix comprises polyethylene terephthalate, and wherein the UV absorbing composition comprises polyethylene naphthalate and a polyoxyalkylene UV absorber, comprising:

combining the polyester matrix with the polyethylene naphthalate and the polyoxyalkylene UV absorber, and mixing thoroughly the resultant composition, such that the composition contains less than 2000 ppm by weight of the polyoxyalkylene UV absorber and the polyoxyalkylene UV absorber conforms to the structure represented by Formula (I)

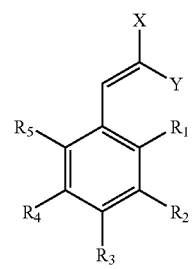

(I)

wherein $R_1$, $R_2$, $R_3$, $R_4$, and $R_5$ are the same or different and are selected from the group consisting of $C_{1-20}$ alkyl, halo, hydroxyl, hydrogen, cyano, sulfonyl, sulfo, sulfato, aryl, nitro, carboxyl, $C_{1-20}$ alkoxy, and B-A, wherein at least one of $R_1$, $R_2$, $R_3$, $R_4$, and $R_5$ is B-A, wherein B is selected from the group consisting of N, O, S, $SO_2$, $SO_3$, $CO_2$, and A is represented by the Formula (II)

[polyoxyalkylene constituent]$_2$R'      (II)

wherein 'polyoxyalkylene constituent' is selected from the group consisting of at least three monomers of at least one $C_{2-20}$ alkyleneoxy group, glydicol, glycidyl, or mixtures thereof, R' is selected from the group consisting of hydrogen, $C_{1-20}$ alkoxy, $C_{1-20}$ alkyl, and $C_{1-20}$ esters; wherein if B is N, then Z is 2, and if B is other than N, then Z is 1; X and Y are the same or different and are selected from the group consisting of hydrogen, cyano, C(O)OR, C(O)R, C(O)NR"R'", $C_{1-20}$ alkyl, and $C_{1-20}$ alkoxy, or X and Y are combined to form a ring system, and R, R", and R'" are defined as above for any of $R_1$, $R_2$, $R_3$, $R_4$, and $R_5$; and wherein if X and Y are not combined to form a ring system then at least one of said X and Y is either cyano or hydrogen.

18. The method of claim 17, wherein the polyethylene naphthalate and the polyoxyalkylene UV absorber are added to the polyester matrix separately.

19. The method of claim 18, wherein the polyethylene naphthalate and the polyoxyalkylene UV absorber are added simultaneously to the polyester matrix.

20. The method of claim 18, wherein the polyethylene naphthalate and the polyoxyalkylene UV absorber are added sequentially to the polyester matrix.

21. The method of claim 17, wherein said polyethylene naphthalate and the polyoxyalkylene UV absorber are added to said polyester matrix prior to completion of polymerization of the polyester matrix.

22. The method of claim 17, wherein said combining step is performed by adding the polyethylene naphthalate and polyoxyalkylene UV absorber to a plurality of pellets formed from the polyester matrix, and wherein said mixing step is a melt mixing of the composition.

23. The method of claim 22, wherein said melt mixing is performed in a twin screw extruder.

24. The method of claim 17, wherein said combining step is performed by adding the polyethylene naphthalate and polyoxyalkylene UV absorber to a melt formed from the polyester matrix.

25. The method of claim 24, wherein said mixing step is a melt mixing of the composition.

26. The method of claim 25, wherein said melt mixing is performed in a twin screw extruder.

27. The method of claim 17, wherein said combining and mixing steps are both performed in a twin screw extruder.

* * * * *